(12) United States Patent
Havira et al.

(10) Patent No.: US 6,516,668 B2
(45) Date of Patent: Feb. 11, 2003

(54) AUTOMATIC CARRIAGE ALIGNMENT

(75) Inventors: Robert Mark Havira, New Fairfield, CT (US); Joseph S. Bakach, Jr., Bridgeport, CT (US)

(73) Assignee: Harsco Track Technologies, Inc.

( * ) Notice: Subject to any disclaimer, the term of this patent is extended or adjusted under 35 U.S.C. 154(b) by 0 days.

(21) Appl. No.: 09/754,647

(22) Filed: Jan. 5, 2001

(65) Prior Publication Data

US 2001/0032513 A1 Oct. 25, 2001

Related U.S. Application Data

(60) Provisional application No. 60/174,520, filed on Jan. 5, 2000.

(51) Int. Cl.[7] .............................................. G01N 29/04
(52) U.S. Cl. ................ 73/636; 73/634; 73/639
(58) Field of Search ........................ 73/628, 633, 634, 73/635, 636, 639

(56) References Cited

U.S. PATENT DOCUMENTS

| | | | |
|---|---|---|---|
| 4,165,648 A | 8/1979 | Pagano | 73/625 |
| 5,020,371 A | 6/1991 | Panetti | 73/636 |
| 5,339,692 A | 8/1994 | Shoenhair, et al. | 73/636 |
| 5,419,196 A | 5/1995 | Havira et al. | 73/636 |
| 5,578,758 A | 11/1996 | Havira et al. | 73/636 |
| 5,804,731 A | * 9/1998 | Jaeggi | 73/636 |
| 5,987,991 A | * 11/1999 | Trantow et al. | 73/624 |

* cited by examiner

Primary Examiner—Richard A. Moller
(74) Attorney, Agent, or Firm—St. Onge Steward Johnston & Reens LLC

(57) ABSTRACT

An ultrasonic aligning device for laterally aligning a rail testing device with respect to a rail has an ultrasonic transducer formed of an array of closely spaced ultrasonic elements, with center to center distances between elements being selected to determine incremental lateral positions of the array relative to the rail. The ultrasonic elements are selectively actuated to cause the generation of ultrasonic beams towards the base portion of the rail. Reflections from the base portion are detected to produce reflection signals representative of the incidence of the ultrasonic beam onto said base portion. The reflection signals are processed by a reflection analyzer for a determination of the lateral offset of the ultrasonic array relative to the rail. A position signal indicative thereof is produced and used to laterally displace the array to achieve a desired lateral alignment of the rail testing device with the rail.

20 Claims, 9 Drawing Sheets

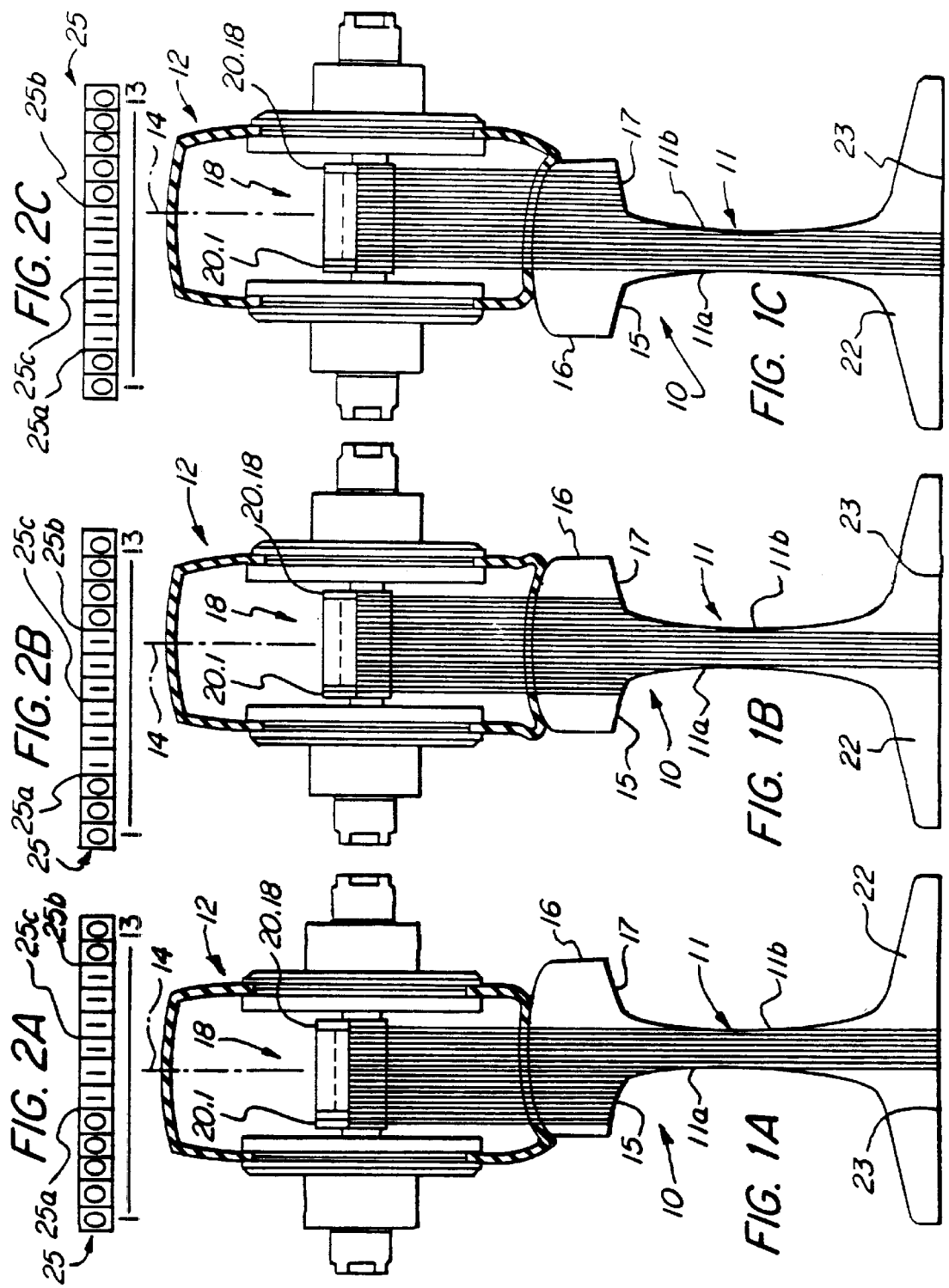

AUTOMATIC CARRIAGE ALIGNMENT

PRIOR APPLICATION

This application claims the benefit of Provisional Application Ser. No. 60/174,520 filed Jan. 5, 2000 and entitled Transducer Array Control Board and this prior application is incorporated herein by reference thereto.

FIELD OF THE INVENTION

This invention generally relates to ultrasonic testing of railroad rails and further relates to an apparatus and method for maintaining an ultrasonic rail investigating tool in vertical alignment with a rail during testing of that rail. More specifically this invention relates to an apparatus and method that detects the middle of a rail and generates a signal indicative thereof for aligning a rail investigating tool.

BACKGROUND OF THE INVENTION

Periodic rail maintenance is vital to the normal performance of railway systems and typically includes complicated procedures. Thus, the rail should be inspected for faults and, particularly, for a proper shape, which has to be ascertained to determine whether various rail parameters are within specified acceptable tolerances, or whether the rail should be condemned.

A variety of methods are currently employed to conduct the tests directed to determine external and internal defects of the rails on site. One non-destructive testing method is the ultrasonic testing of a rail. This technique consists in bringing an emitter, receiver or emitter/receiver transducers in contact with the head of the rail, the orientation of which is adapted to the type of flaws to be detected. More particularly, ultrasonic rail testing involves the examination of a wide range of rails some of which have their gauge or head worn down vertically or laterally or both. U.S. Pat. No. 5,419,196 shows one type of ultrasonic testing device for examining a rail.

Ultrasonic transducers used to examine rails may become laterally shifted from the center of the rail so that some transducers employed in the investigating tool are not employed in their optimum position.

During in-situ testing of rails, the transducers typically are mounted on carriages, which roll on top of the rails to maintain the transducers in sonic contact with the rail. Such a testing system includes transducers mounted in a wheel which rolls on the rail, the sonic contact between the transducer and the rolling surface being realized for example by a liquid contained in the wheel as described in U.S. Pat. No. 4,165,648 to Pagano. It is desirable that a proper lateral or transverse positioning of a probe wheel relative to the rail on which the wheel is moved is established for optimum performance.

Techniques for aligning a rail testing carriage on which ultrasonic test equipment is located are known. See, for example, U.S. Pat. No. 4,044,594 to Owens et al. In this patent a rail mounted carriage supports ultrasonic test equipment and is provided with lateral carriage adjustment devices so that the ultrasonic rail test equipment can be maintained in lateral alignment with the rails. This equipment depends upon the use of a guide that runs along the side of the rail gauge to sense its location and thus enable a lateral alignment with respect to that side of the gauge head. This approach depends upon the side of the rail gauge to maintain its normal position relative to the web of the rail. However, if there is wear on that side, lateral adjustment loses its accuracy and alignment becomes less precise.

U.S. Pat. No. 5,020,371 to Panetti (Panetti '371) describes a device to determine the plane of symmetry of a rail by bouncing ultrasonic pulses off the undersides or fish plates of a rail. This technique assumes that it is independent from wear problems of the head of the rail. However, rails are prone to wear unevenly so that reliance upon the travel times of ultrasonic pulses from the fishplates to derive lateral alignment of the ultrasonic rail testing transducers is prone to errors.

Particularly, Panetti '371 discloses a method of positioning a member with respect to the symmetry plane of a rail and emitting through the rail's head two diverging ultrasound beams, each of which is propagated perpendicular to and ricocheted from a respective one of the rail's fish plates. Upon determining the time difference between the emission and the reception of the echo signal for each of the ultrasound beams and comparing this echo signal with a reference value, a control signal correcting the transverse positioning of the member is generated.

The Panetti system, however, is based on a complicated system of determining and comparing different signals and premised on the notion that the fish plates are perfectly symmetrical to the axis of symmetry of the rail and not subjected to wearing off. As a consequence, the transducers ought to be inclined at the same angle as the fish plates in order to properly determine the deviation from the rail's axis of symmetry. In reality, however, due to the variations in the dimensions of the rails, misalignment of the abutting ends of the adjacent rails and the angle variation between the fish plates as well as between the transducers, the ultrasonic coupling between the wheel and the rail's head may not be entirely precise.

U.S. Pat. No. 5,339,692 to Shoenhair et.al discloses a device for locating a web centerline with an array of symmetrically positioned transducers each transmitting and receiving ultrasound signals bounced from either the base or the underside of the rails. The reflected signals are compared to a signal generated by a centrally positioned transducer. As a consequence, if the compared signals have different amplitudes, then a control signal is generated to actuate a means for lateral displacement of a controlling member relative to the rail.

The Shoenhair device has a complicated control system designed to process a plurality of signals, particularly those that bounce from the underside of the rail's head. As a consequence, the control system may be prohibitively expensive. Also, this device may not be indicative of the actual position of a wheel with respect to the centerline of the rail because transducers receive echoes reflected from a wide segment of the rail including the slanted surfaces of the railhead. To obtain valid information of the wheel's position with respect to the rail centerline using echoes from the underside surfaces of the railhead, the transducers have to be properly aligned with these surfaces. However, it has been found difficult to achieve such alignment due to variations in the loading of the wheel, variations in the rolling radius of the wheel, the size of the flat and its position relative to transducers positioned above the underside surfaces of the railhead. Furthermore, a heavily loaded wheel has a tendency to act somewhat as a squeegee and force the coupling fluid from the sides of the tread thereby primarily affecting the acoustic coupling between the transducers and the underside surfaces of the railhead.

It is, therefore, desirable to provide an automatic carriage alignment system employing using ultrasonic transducers in a precise and reliable manner.

SUMMARY OF THE INVENTION

With an automatic carriage alignment system in accordance with the invention a plurality of ultrasonic beams are obtained from an array of ultrasonic transducers that is laterally aligned transverse to the rail. The beams are formed by selectively pulsing successive predefined groups of ultrasonic elements in the array to produce echo signals from beam reflections from the rail's base. An echo analyzer responsive to the echo signals is used to derive the lateral position of the array of ultrasonic elements with respect to the centerline of the rail and generate a signal to activate an actuator with which an ultrasonic rail-investigating wheel can then be aligned with the rail.

The reflection analyzer registers signals representative of hits and non-hits from ultrasonic beams with the rail base from successive laterally spaced groups of elements. The hits and non-hits define an edge of the web of the rail and enable one to fix the position of the array relative to the rail. In a preferred mode the center for the array is aligned with the center of the rail. However, other edges can be aligned and if necessary an offset introduced to relate a reference line in the array with a reference line on the rail. A correction signal is generated when the derived lateral position is deemed off-center and is used to correct the lateral alignment of the carriage on which the wheels with their ultrasonic rail investigating transducers are located.

As described in one embodiment of the invention the base hits are detected when an echo signal exceeds a certain threshold. A hit and non-hit data pattern is stored and evaluated to produce a correction signal indicative of the position of the center of the array relative to the centerline of the rail. The correction signal is applied to wheel actuators to displace the carriage so that the centers of ultrasonic wheels used to investigate the rails have a desired alignment with the centerlines of the rails.

As described herein for one embodiment of the invention an initial transducer array control (TAC) provides the electronic circuitry to perform testing of an alignment algorithm and its implementation. The TAC operates ultrasonic transducers in three different modes: constant, scanning and/or alignment.

In the constant mode the TAC may continuously pulse a selected group of N transducers. The scanning pulsing mode is characterized by simultaneously pulsing one (1) through N consecutive transducers of the array, store any hit data in RAM and then pulse N consecutive transducers beginning at transducer 2. The scanning continues until the last N consecutive transducers are pulsed which is particularly useful for calibration purposes. As a result of the calibration, a particular pattern of LEDs can visually inform an operator that the alignment wheel is properly aligned.

In the alignment mode the TAC scans the array to, analyze the data for validity and command a carriage control to move the carriage in accordance with the evaluated data. The alignment algorithm assumes that the center of the array is aligned with the center of the zero degree transducer mounted within each one of two probe wheels, each of which is aligned with a pair of alignment wheels. Other assumptions can be used and can include use of an offset. The key feature is that the array's position within the probe wheel is known.

It is, therefore, an object of this invention to provide an improved automatic carriage alignment system and method for maintaining a rail investigating tool in lateral alignment with a rail.

It is another object of this invention to provide an automatic carriage alignment system and method that provides a reliable and automatic centering technique for a carriage carrying an ultrasonic rail investigating tool located within a wheel that travels over a rail in proper lateral alignment with the rail.

Yet another object of the invention is to provide an automatic carriage alignment system carrying a rail investigating tool by using those echoes that are reflected from the base of the rail.

Still another object of the invention is to provide an automatic carriage alignment system capable of evaluating echo signals received from the base of the rail in order to generate a control signal to activate a carriage actuator which can laterally displace the carriage to a position which establishes a desired alignment of a rail investigating tool, located on the carriage, with respect to the centerline of the rail.

BRIEF DESCRIPTION OF THE DRAWINGS

The above and other objects, features and advantages will become more readily apparent from the following specific description of the invention accompanied by the following drawings, in which:

FIGS. 1A and 1C are front sectional views of a probe wheel housing an array of ultrasonic elements and shown in first and second misaligned positions, respectively, wherein the centedines of the probe wheel and rail are laterally offset.

FIG. 1B is a front sectional view a probe wheel housing an array of ultrasonic elements and shown in an aligned position, wherein the centerlines of the wheel and rail below the probe wheel coincide with one another.

FIGS. 2a–2c are matrices of base hits indicating the probe alignment with aligned and laterally offset positions.

DETAILED DESCRIPTION OF THE DRAWINGS

Figure 6:
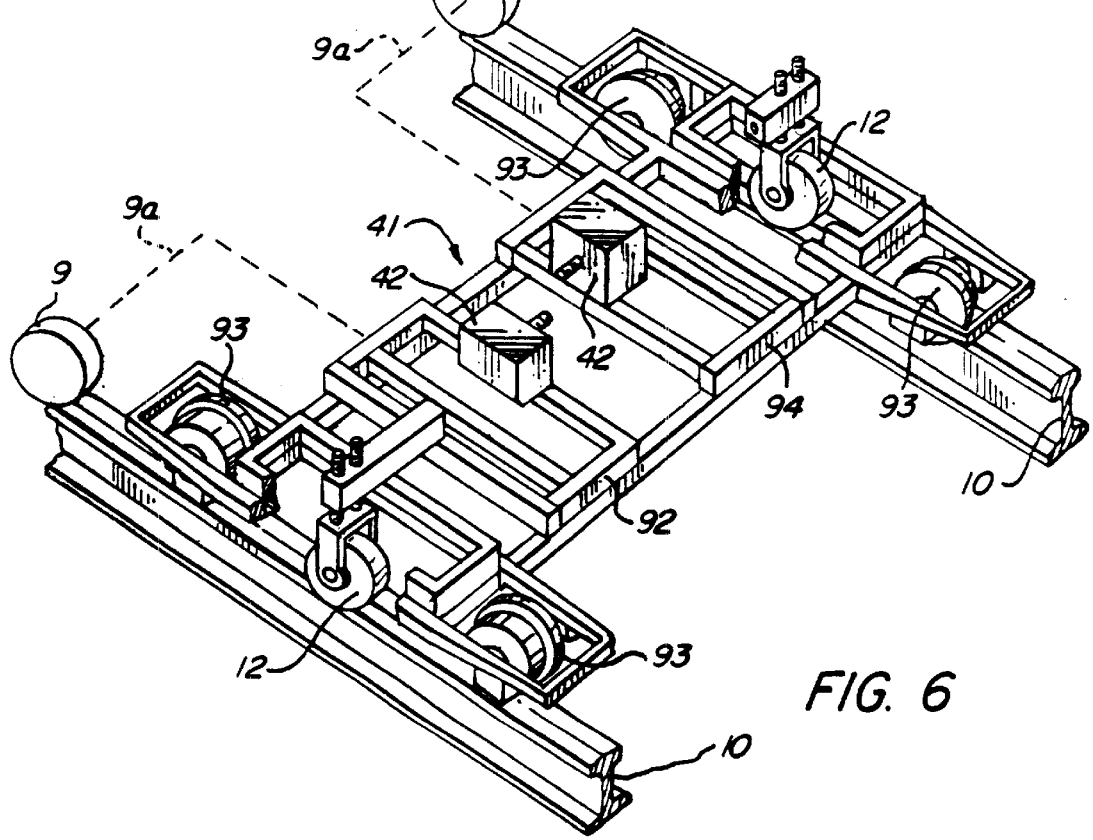
FIG. 6 is a perspective view of the alignment system in accordance wit the invention.

Referring to FIGS. 1a–1c and 6, the invention involves maintaining ultrasonic rail investigating wheels, such as 9, in proper lateral alignment over a rails 10. Such rail investigating wheels enable an inspection of a rail 10 in a manner as shown and described in U.S. Pat. Nos. 5,578,758 and 5,419,196 to Mark Havira et al and owned by the same Assignee as for this invention and incorporated herein by reference thereto. It is desirable that these wheels 9 remain centered over the rail 10 being investigated. This requires that a lateral adjustment of the rail-investigating wheels be made. Lateral adjustments can be made by mounting the wheels 9 on a laterally adjustable carriage 41 as illustrated in FIG. 6.

In FIG. 6 a laterally adjustable rail carriage 41 carries ultrasonic testing devices such as sensing probe wheels 9, at least one for each rail 10. The attachment of wheels 9 is as suggested by dotted lines 9a interconnecting to outer frames 92, 94. The frames 92, 94 in turn are supported by railroad wheels 93, which are located on rail tracks 10. The frames 92 and 94 are individually laterally movable relative to wheels 93. The testing devices can be standard ultrasonic rail investigating wheel 9 as described in the aforementioned U.S. Patents to Havira. The frames 92, 94 also each carry an alignment sensing probe wheel 12. The frames 92, 94 are individually and laterally displaceable by hydraulic actuators 42.

The invention relates to a technique to determine how much of a lateral adjustment is to be made to center or establish a desired lateral position of wheel probes 12 and thus also the rail investigating wheels 9, over rails 10. The invention involves an ultrasonic probe alignment wheel 12, with a yoke assembly and membrane 21 for enclosing ultrasonic transducers in a manner as described in the aforementioned patents to Havira.

The wheel probes 12 each include an ultrasonic array 18 formed of transducer elements 20 directed to produce ultrasonic beams 19 downwardly through the flat spot of an enclosing membrane 21 into the head 16 of rail 10. The ultrasonic beams 19 are intended to hit the bottom rail interface 23 from which an acoustic reflection is returned to the transducers 20 acting as detectors. The detected reflections indicate that the emitting transducer elements 20 are located opposite the web 11 of rail 10 while an absence of the detection of reflections after the emission of an acoustic beam pulse indicates that the emitting transducers are too far off-set from the center of the rail 10 to cause a reflection from the base interface 23.

Elements 20 are uniformly spaced from one another at a fixed distance, for example ⅟16", and each element is a zero degree element made either of lead metaniobate ceramic or a PZT material. The latter material has a considerable gain advantage over lead metaniobate and, since the area of interest is only the one surrounding the base part of a rail, PZT material is preferred.

When the detected reflections are from array elements 20, which are located near the center of the array 18, the wheel 12 is deemed to be in alignment with the rail 10 as illustrated in FIG. 1b. When the detected base reflections are from elements primarily located on either the left side as shown FIG. 1a or primarily from elements located on the right side of the array 18 as shown in FIG. 1c the wheel is deemed to be off center and a lateral carriage adjustment is needed to center the wheel 12 with respect to rail 10.

The basic premise of the invention is that only echo signals representative of acoustic reflections off the rail's base 22's interface 23 are received and processed. Other echo signals such as those reflected by the undersides 15 and 17 of the rail's head 16 are ignored.

The invention is graphically illustrated in a matrix 25 in FIGS. 2a–2c. Matrix 25 represents the presence or absence of hits of ultrasonic beam pulses on the base interface 23 from activation of successive ultrasonic elements 20 in array 18. The transducer array 18 is shown to consist of a predetermined number of elements 20, for example eighteen (18), though a different number can be employed.

In the illustrative embodiment the elements 20 are activated or "scanned" in successive groups of six elements, though a different number of elements in a group can be used. This means that six elements 20 are simultaneously activated to produce acoustic ultrasonic beams 19 directed at the railhead 16. The number of elements 20 in a group can vary with a larger number being used to increase the resolution though with a lower beam power from any one of the elements because these would tend to become smaller. When fewer elements such as four are used in a group, the beam power from any one of the elements can be increased, though the resolution that can be obtained in centering the wheel 12 relative to rail 10 tends to be less.

With a total of 18 elements 20 in the array 18 there are thirteen successive groups of elements. The matrix 25 has its locations numbered 1 through 13, from left to right. When a reflection from the interface 23 is detected by an element 20, this is recorded as a "hit" and is identified as a one in the matrix 25 while absences of a reflection are registered as a zero. As successive groups of elements 20 are activated and used to receive or detect reflections, the recorded "hits" or "ones" as well as absences of "hits" or "zeroes" are stored in a memory of a signal processor as a function of the group of elements to which the ones and zeroes relate. The stored values of the elements activations can then be used to derive the center of the rail relative to wheel 12 or relative to some fixed axis such as 14 of wheel 12 because the location of the elements 20 relative to center axis 14 is known.

As further described herein, a search is made for the sides 11a and 11b of web 11 by detecting the corresponding boundaries between "ones" and "zeroes" in the values from the elements 20 and noting the positions that these boundaries represent. Once these boundaries are determined, the center of the rail 10 is determined as one half of the difference between the positions of the boundaries. Alternatively, the alignment of the wheel 12 with the center of the rail 10 can be derived from the detection of an equal number of zeroes on both sides of a consecutive group of hits or ones.

In the views of FIGS. 2a–2c the ideal number of hits are shown for each activation of a group of elements 20, i.e. six hits. In practice, the number of hits in a group may be less than the number of elements 20 in the activated group. A test is then used to determine whether the stored values can be used or are valid for deriving the relative position of wheel 12 to rail 10 and if so, whether the left side 11a or right side 11b of web 11 is represented by the boundary between consecutive hits and consecutive non-hits or absences of hits. When an element 20 occupies a position above an underside 15 of the railhead 16 no base echo is received.

Turning to FIGS. 1A and 1C, the probe wheel 12 is displaced from the ideal position respectively to the left and right of railhead 16. This is indicated from the hits obtained from certain groups of elements. Thus, hits registered by elements 2 through 8, as shown in FIG. 2C, indicate that the probe wheel 12 has been displaced to the right. Similarly FIG. 2A indicates a displacement of the probe wheel 12 to the left. The amount of displacement can be determined by detecting where in the matrix 25, shown in FIG. 2a, there is a transition, such as at 25a and 25b, from a consecutive group of ones to a consecutive group of zeroes. This identifies the left side boundary of web 11 and thus one specific distance, one half of the web thickness, from the center of the web 11.

A preferred technique for determining the relative position of the array 18 relative to the rail 10 is by selecting an array 18 that is larger in length than the thickness of the web 11. Then there will be at least one set of hits that indicates the full width of the web 11 and the center of the hits is commensurate with the center of the rail 10. Thus, in FIGS. 2A–2C the center of the rail is located opposite the location 25c in the array 18. This location is offset in FIGS. 2A and 2C and can be determined by the computer in which the hits are stored as a function of elements 20.

The amount of lateral carriage adjustment needed is determined by the lateral location of either the measured center position 25C or by using the transitions 25a and 25b in FIG. 2a that identify the boundaries 11a and 11b. Assuming that each hit from an element is indicative of a predetermined lateral distance, for example 1/16 of an inch, then the signal processor can determine that the alignment wheel 12 in FIG. 2a has been shifted to the left by an amount of two spacings between elements 20 or in the specific embodiment 1/8 of an inch. A similar determination can be made with lateral offset to the right as shown in FIG. 2C or a zero offset in FIG. 2b.

The placement of the array 18 within the alignment probe wheel 12 is done so that the signal processor has precise information as to the lateral location of the array 18 and elements 20. The vertical distance of array 18 above the top of the railhead 16 is preferably set at a distance from the railhead 16 that reduces interfering secondary echoes from rail 10, with a distance of preferably at least about 3 inches being acceptable. The number of elements 20 in anyone lateral distance increases the precision of determination of the lateral location of wheel 12 relative to the rail's centerline.

Figure 3:
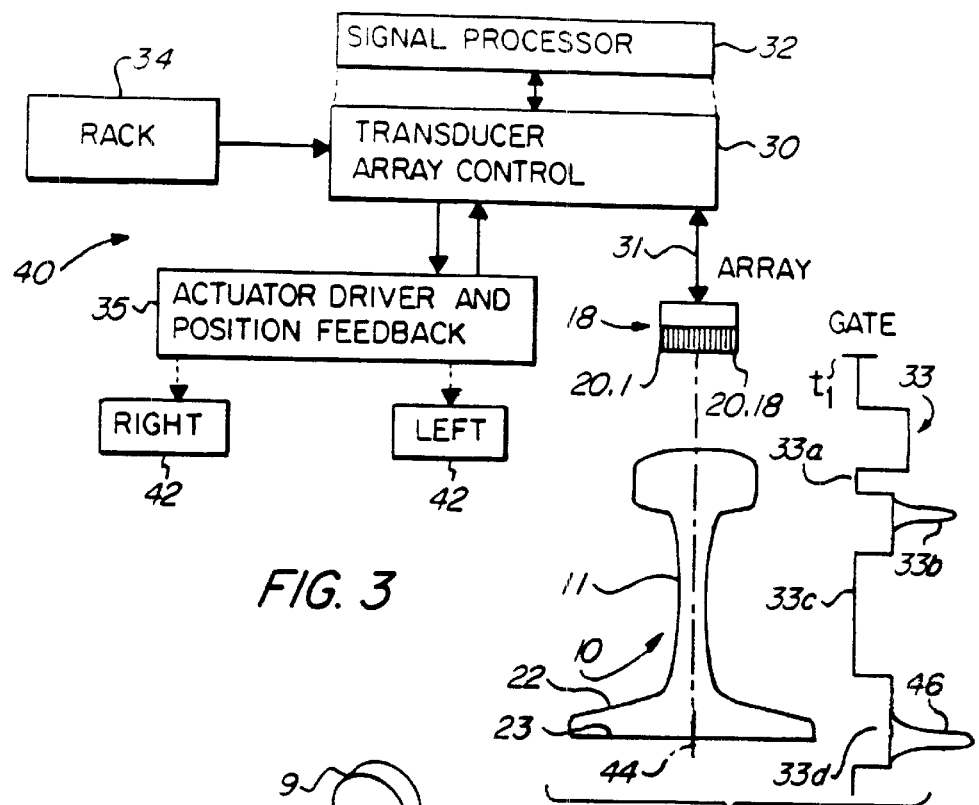
FIG. 3 is a schematic view of a control alignment system in accordance with the invention.

FIG. 3 shows an apparatus 40 for determining the lateral location of an array 18 relative to a rail 10. The apparatus 40 includes a transducer array control (TAC) 30 including a signal processor 32. The TAC 30 may be a stand-alone circuit board, which receives power from a rack 34 equipped with on-board voltage regulators and DC converters supplying the power requirements for the equipment.

The TAC 30 employs an automatic scanning mode in which it scans the elements 20 in array 18 by first generating an activating pulse on line 31 for an element 20 and then switching to a receiving mode on the same line 31 to detect a reflection such as 46 from the base interface 23. Consecutive elements 20 are so activated and monitored. Reflections 46 are received by those ultrasonic elements 20 positioned in alignment with the web 11 and the portion of the base 22 below web 11.

As illustrated with the timing waveform 33 in FIG. 3, the TAC 30 initiates a pulse to an element 20 at time t1. During then the time represented by pulse 33a reflections on the output line of the element are detected and passed onto the signal processor 32 to utilize reflections from the top surface of the railhead 16. Reflections 33b from the underside surfaces 15 and 17 of railhead 16, see FIGS. 2a–2c, are passed through. Then a gate 33c is applied to mask signals from the element for a time period equivalent to most web 11 heights, while reflections 46 from the base interface 23 are detected and passed onto signal processor 32 during a gate time interval 33d. Gating circuits and techniques are well known in the art related to ultrasonic non-destructive testing.

Hence, apparatus 40 produces signals indicative of the amount of mis-alignment of the center line 14, see FIGS. 1a–1c, of the array 18 of transducers 20, with respect to the portion of the base 22 below the web 11 or the rail's centerline 44. The signal processor 32 with the TAC 30 then derives signals indicative of the lateral offset of array 18 with respect to the rail head centerline 44 and produces, when needed, correction signals that are applied to a control 35 to drive hydraulically operated actuators 42 to move the carriage 41 in a direction that re-aligns it with the railhead centerline 44.

Figure 4:
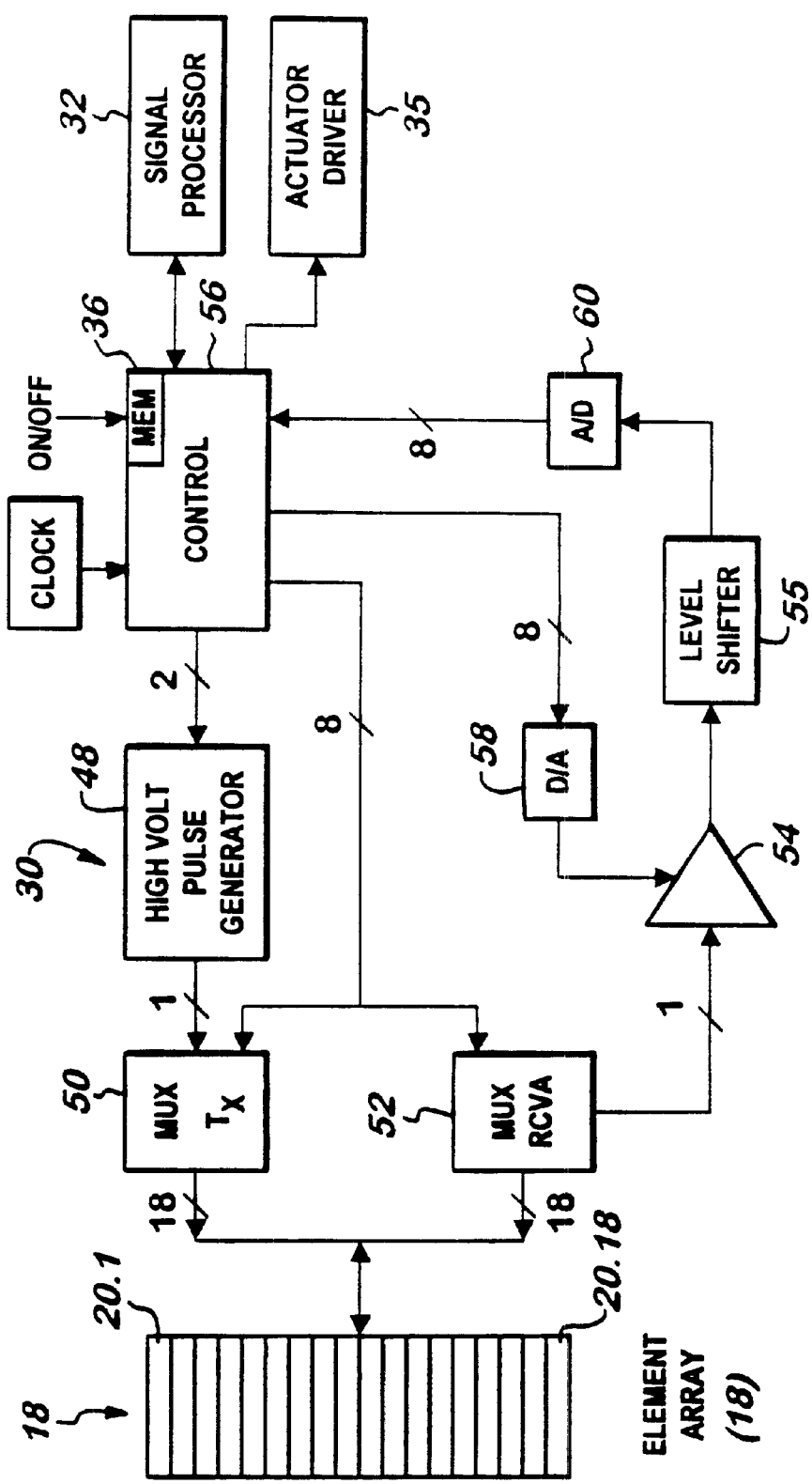
FIG. 4 is a basic block diagram of a transducer array control (TAC) of the carriage alignment device in accordance with the invention.

Referring to FIG. 4, the TAC includes devices are well known in the art to activate and then receive echoes or reflections. For illustration purposes, since other devices and techniques can be used, the TAC is shown to include a pulse generator 48, which delivers pulses to activate ultrasonic elements through a multiplexer 50. Acoustic reflections caused by a pulse are passed through multiplexer 52 to an amplifier 54 and thence through a level shifter 55 to an analog to digital converter 60. Control of the multiplexers 50, 52, the gain of amplifier 54 is by a digital controller 56 having a memory 36. Power is supplied by equipment on a rack 34. The control operates to activate groups of elements 20 at one time. Thus, for example, six or another number of elements 20 are activated be enabling as many output lines from the multiplexer 50 to be coupled to the input pulse from pulse generator 48.

Figure 5:
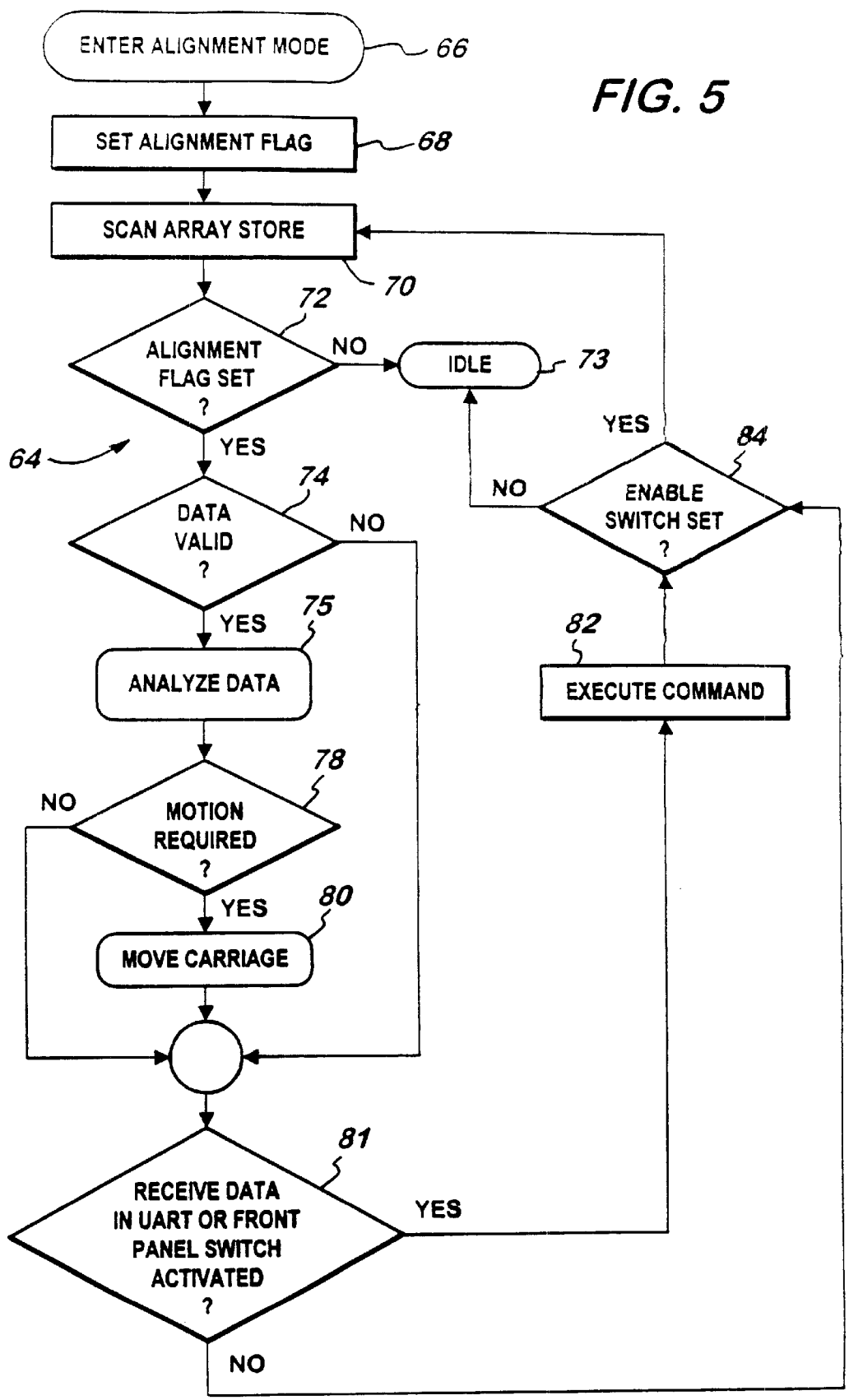
FIG. 5 is a flow chart illustrating a basic alignment algorithm flowchart for valid base.

FIG. 5 illustrates one technique 64 for carrying out the ultrasonic wheel alignment correction in accordance with the invention. The technique includes programming steps within the computer 32 and within the TAC control 30. At 66 an alignment mode is entered. An alignment flag is set at 68 to commence scanning of the array 18 of ultrasonic elements 20 at 70.

The TAC scans array 18 by firing groups of consecutively placed emitters 20 one group at a time. Echoes reflected from base interface 23 of rail 10 are received and digitized and then stored whenever a reflection exceeds a predetermined threshold. The reflection is entered and stored in a signal processor when the timing of the reflection arrives at the emitters 20 within a group and within a gating window timed to detect arrivals from interface 23. The time gate is selected sufficiently wide to accommodate all rail sizes. The times of arrival of reflections from the base interface 23 and their amplitudes are stored in an internal memory for further analysis for each scanned group of ultrasonic elements 20. The amplitude information is not always needed, since a principal purpose of the array 18 is to detect the occurrence of or absence of a reflection from the base interface 23.

If desired, the occurrence and duration for the timing gate for detecting reflections from base interface 23 can be derived experimentally during a calibration mode in which the transducers 20 are activated and times of arrival of the interface reflections recorded and a range for the time gate determined and entered.

The TAC 30, as shown in FIG. 4, causes the activation of successive groups of six consecutive ultrasonic elements 20 at a time. Each group represents a sixteenth of an inch. One complete lateral scan of the array 18 consists of 13 groups or a total lateral distance of about $12/16^{th}$ or 3/4 of an inch. This dimension tends to assure that the lateral dimension of array 18 is as wide or wider than the width of most encountered webs 11. A wider array can be used if larger webs 11 are likely to be encountered. Thus the TAC 30 begins pulsing a first group including, for example, elements 20.1 through 20.6, stores hit and non-hit data for that group in memory and then pulse the next group of six elements and so on until the last group of six elements has been activated and their reflections and non-hits have been recorded.

After the scanning and reflection-storing step 70 has been completed a test is made at 72 whether a carriage alignment needs to be checked. If not a predetermined idle time is entered at 73. If so the data obtained from the scanning step 70 is analyzed at 74 for validity.

Figure 9:
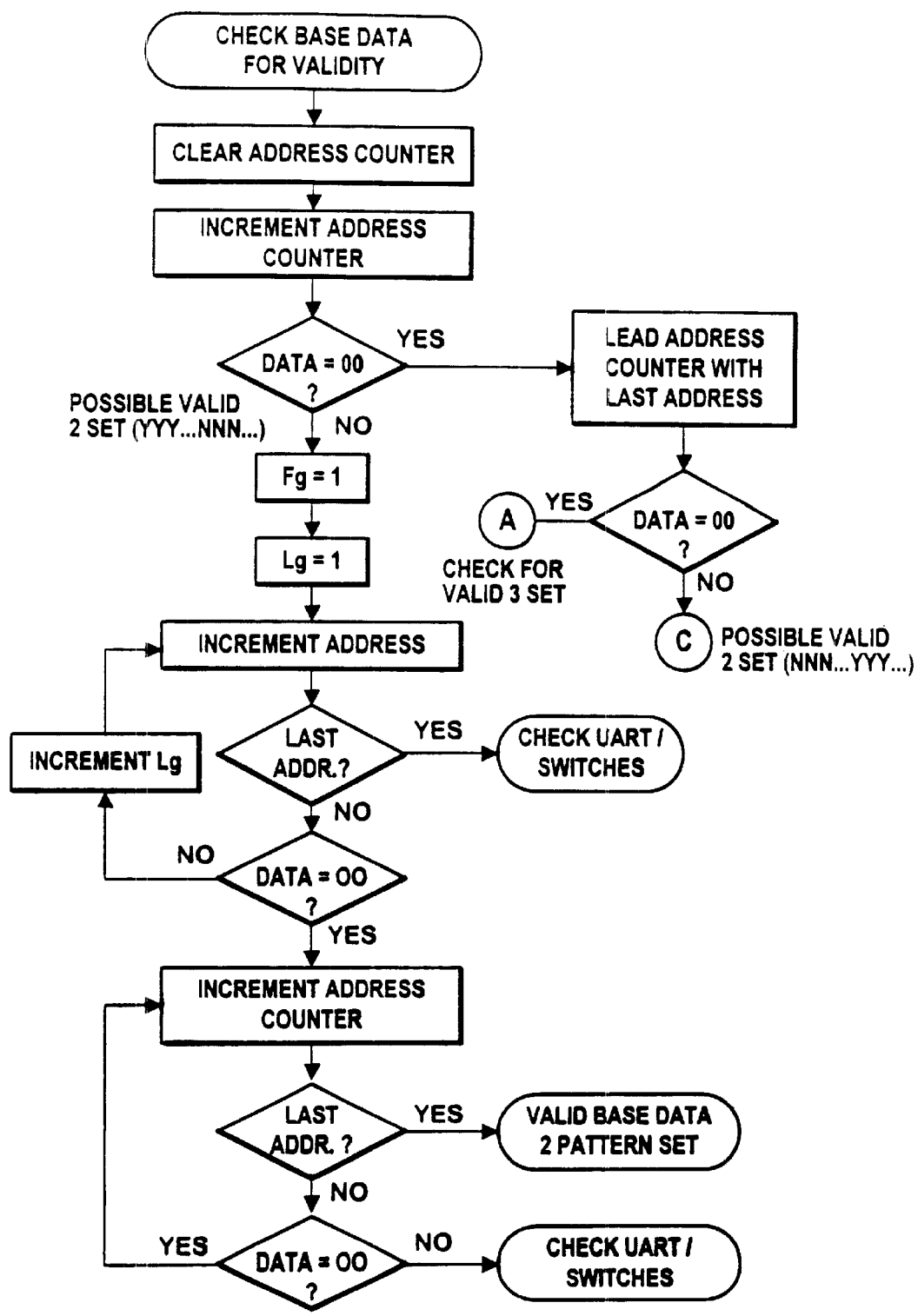
FIGS. 9 through 11 are flow charts of program steps for a data validation procedure used in the reflection analyzer in accordance with the invention.
Figure 10:
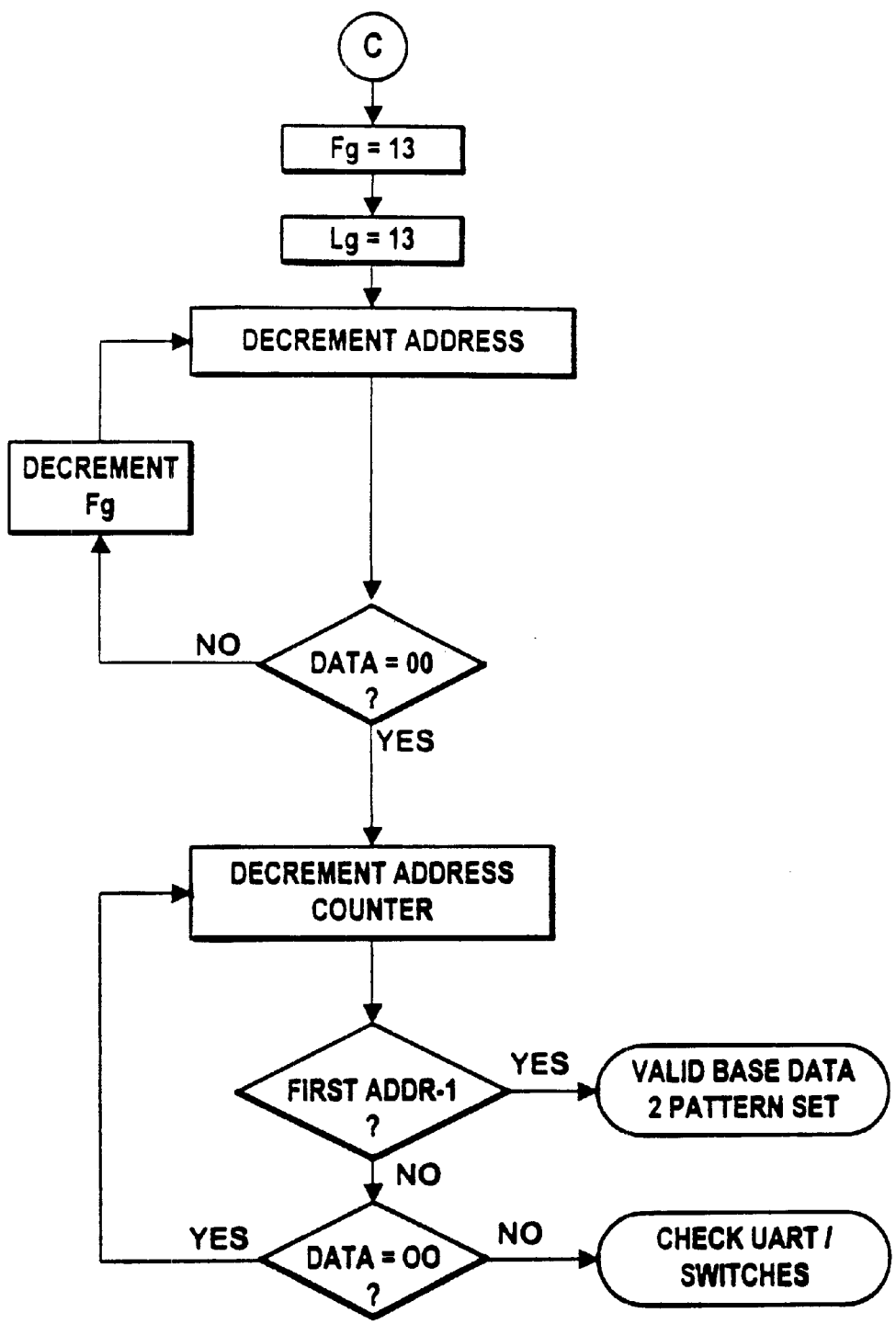
Figure 11:
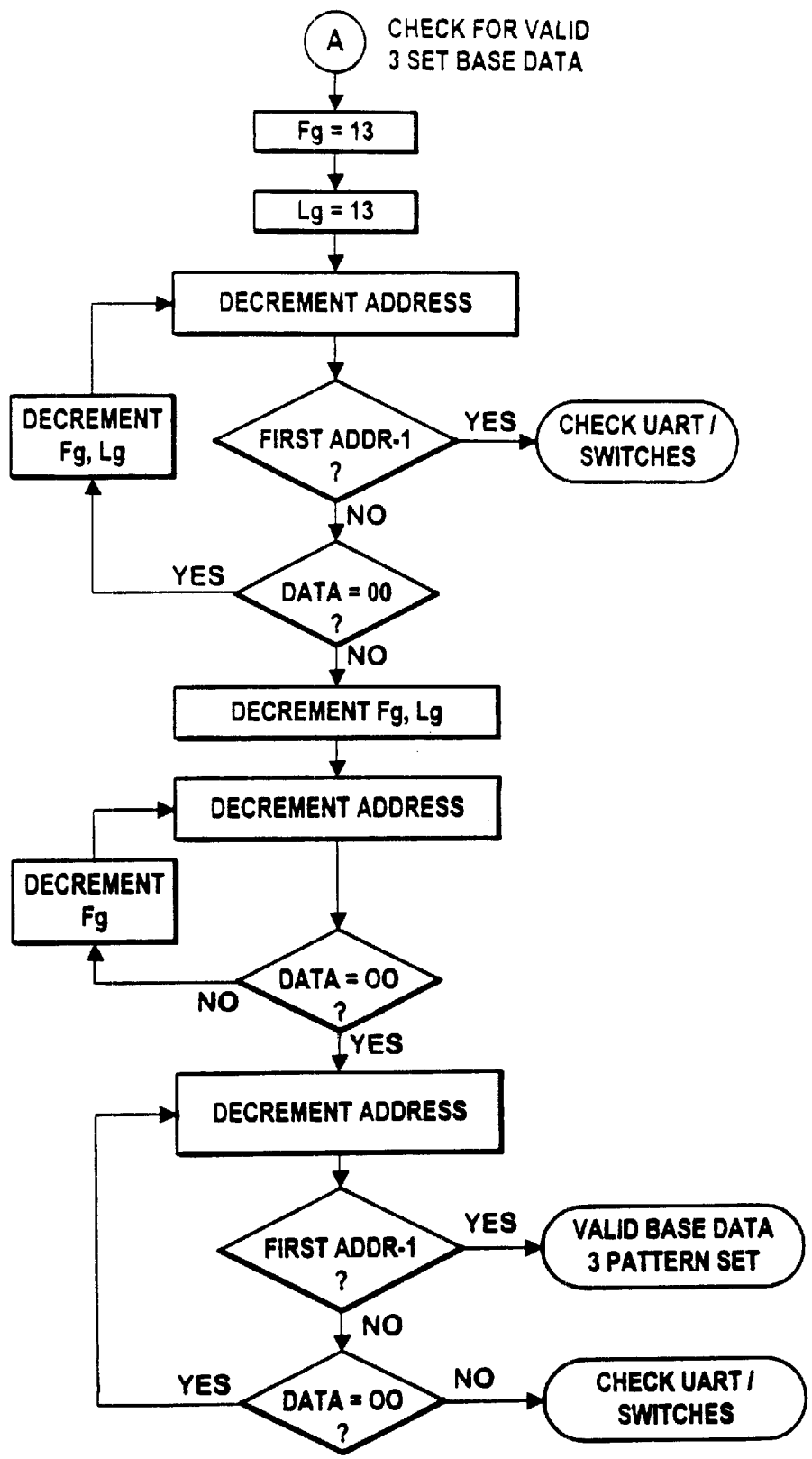

The data from a complete scan of the array 18 involves a check as to whether proper consecutive reflections or a proper absence of reflections have been received. Valid data is determined from an analysis of the patterns as illustrated graphically with the matrices in FIG. 2 and with program steps as shown in FIGS. 9–11. Thus in accordance with one aspect of the invention, valid base data patterns have been defined to consist of consecutive hits, followed by consecutive non-hits; (2) consecutive non-hits, followed by consecutive hits; (3) consecutive non-hits, followed by consecutive hits, followed by consecutive non-hits. Other validation criteria can be set to assure that the data entered from the scanning operation can be used to derive the proper carriage alignment.

If the matrix reveals that an absence of a reflection has occurred as indicated with a zero interspersed between ones in the matrix 25, or a one interspersed between zeroes, the data can be considered as not valid. If the data is invalid, a jump is made in the program to skip the data analysis and lateral carriage movement steps to cause a return to another scanning and storing operation at step 70.

If the data is found to be valid at 74, the data found in a matrix 25 is analyzed at 75 for determining whether a lateral carriage position correction is required. This involves determining where in the matrix data there is a transition from all zeroes to all ones or from all non-hits to all hits and identifying the elements 20 where a transition occurs. If the transition is to the left of the center of the array 18 then the transition is determinative of the left side 11a of web 11. If the transition is to the right of center it is an indication of the right side of web 11. Once a web side 11a or 11b has been detected relative to array 18, in terms of the number of element 20 center-to-center spacings, the lateral position of the array 18 relative to the center line of the railhead 16 or of the web 11 can be derived. A correction signal is then generated representative of the amount, in increments of element-to-element spacings the array 18 is off center.

In a case where the length of the array 18 is greater than the width of the web so that there should be two transitions within a matrix 25 of data, then the program could determine the locations of the two transitions by searching for a series of consecutive ones surrounded by the same number of zeroes on each side of the series of ones for a proper centering of the wheel 12. If there are more zeroes on one side than the other, the carriage needs to be moved to the side yielding fewer zeroes to establish the desired centered position. A correction signal is then produced representative of the number of center-to-center element spacings that the wheel 12 needs to be moved to re-center it over the rail 10.

The result of the analysis step 75 is thus a signal indicative of the amount, in increments of spacings between centers of elements 20, that the array 18 needs to be moved. The correction signal can be modified to the coordinates needed to alter the lateral position of the carriage 41. Hence, at 78 a test is made whether the correction signal is sufficiently large to require a lateral movement of the carriage. If so, the carriage is moved at 80 and if not, the carriage movement is by-passed to step 81.

At step 81 a check is made whether there is a particular front panel instruction that needs to executed If not, a return is made to step 84 to check whether an enabling switch 35 is still on. If not the system is switched to the idle mode at 73. If so, a return is made to the scanning step 70. If the test at 81 indicated that a front panel instruction needs to be carried out, this done at 82.

Figure 7:
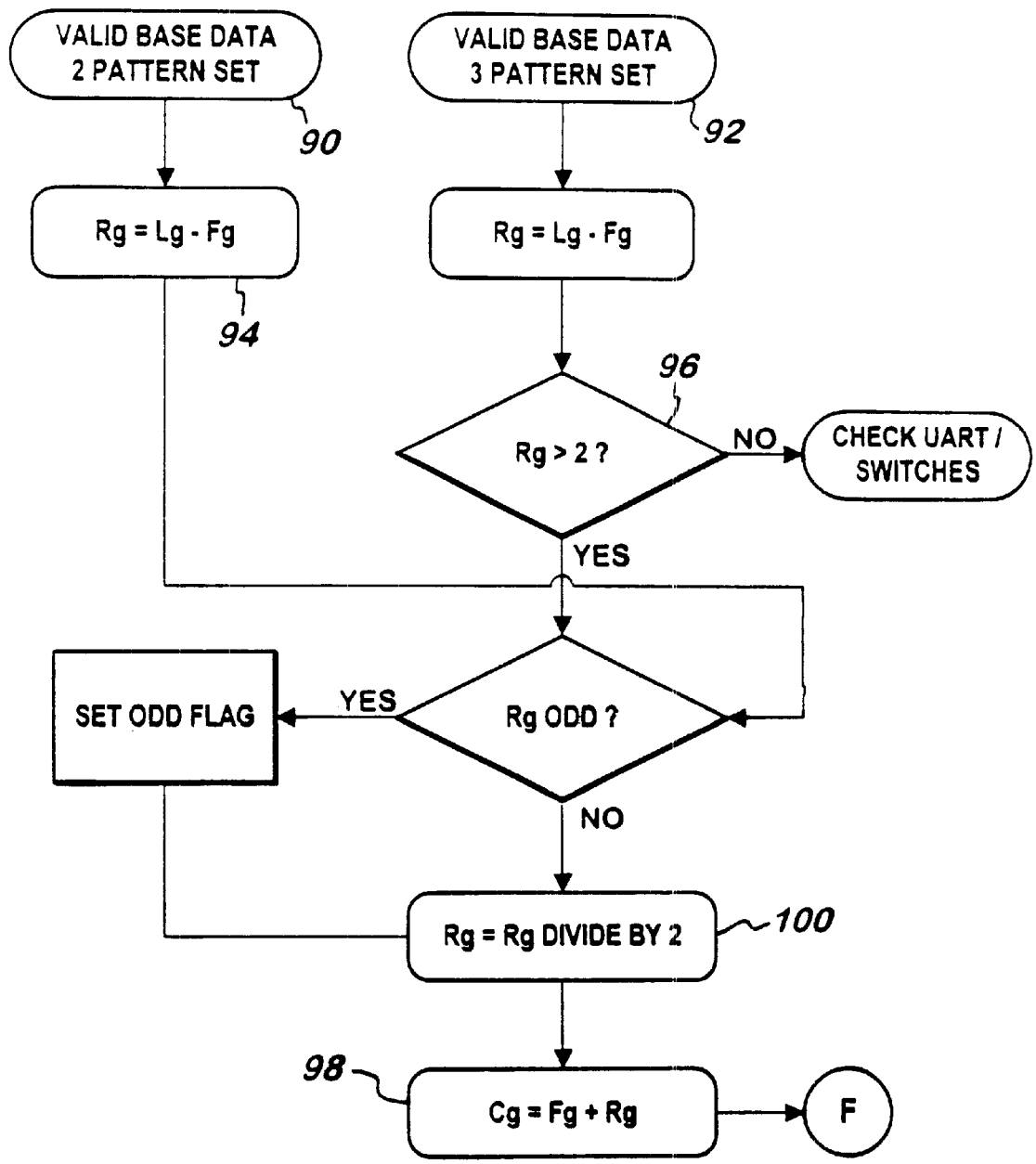
FIGS. 7 and 8 are flow charts for a reflection analyzer in accordance with the invention.
Figure 8:
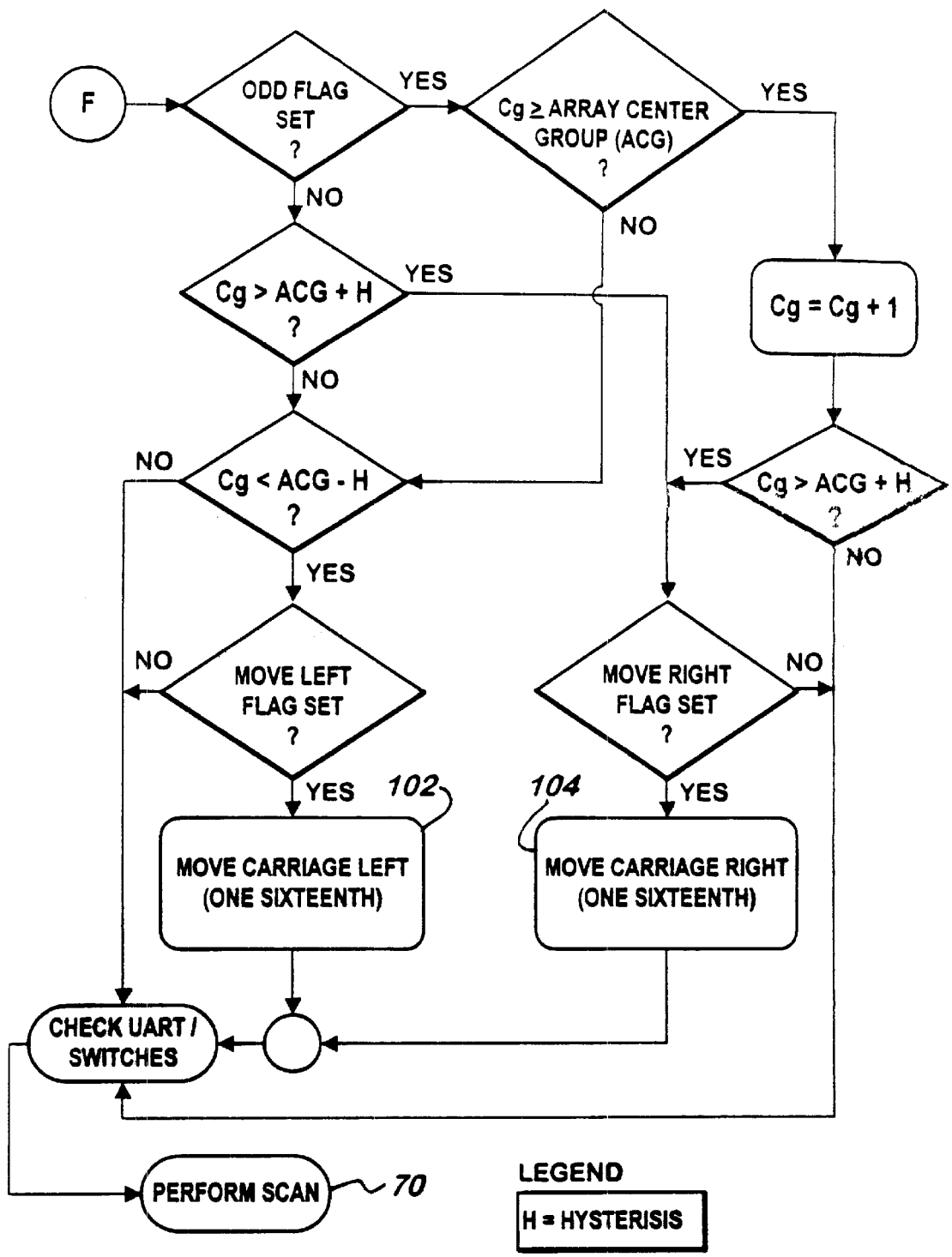

FIGS. 7 and 8 illustrate the analysis step 75 with greater detail together with step 78 used to align the carriage with the rail 10. Thus at 90 and 92 valid base data, as identified during step 74, are identified in two patterns, i.e. whether there is a three pattern set as illustrated in FIG. 2, or a two pattern set using consecutive ones followed by consecutive zeroes or vice versa. In FIG. 7, step 94 determines how many hits there are for a two pattern set and at 96 for a three pattern set. The program steps search out the relative relationship between a center hit or group, number seven, in the array 18 relative to the center 44 of the rail 10. The term group is used to denote the occurrence of a single hit by a group of elements 20. Thus if there are 18 elements 20 in the array 18, then there are 13 groups of six elements, with each group's activation yielding either a hit or a non-hit.

The program searches out the first group (Fg) from one side of the array 18 that yielded a hit and then adding to that, at step 98, one half of the width (Rg), as determined at 100, of the number of consecutive hits. During initial calibration of the ultrasonic wheel 12 the center of the array 18 was aligned with the center of the rail 10, by way of entering the amount of misalignment as an offset into a signal processor or actually physically aligning the array 18 so that the centerlines 14 and 44 lined up.

In FIG. 8 the number of incremental spacings, i.e. the distance between centers of adjacent elements 20, the carriage is to be moved to adjust the lateral position of the wheel 12 is determined. In order to stabilize the lateral motion of the carriage it is only moved at steps 102 and 104 a single increment at a time before another scanning step 70 is commenced. This is done, even though the carriage may need to be moved several increments.

FIGS. 9, 10 and 11 show the validation step 74 with greater detail and implements the rules identified above to be applied to the hits and non-hits during the scanning step 70.

Having thus described one embodiment of the invention its principles and features can be appreciated. Variations from the drawings and description can be made by one skilled in the art without departing from the scope of the invention as determined by the following claims. For example, it is clearly contemplated by the invention that a second array of ultrasonic elements can be used for a detection function, provided the wheel 12 has sufficient room to accommodate the second array. In such case, the second array would be coupled to multiplexer 52 to detect reflections in the manner as described.

What is claimed is:

1. An ultrasonic aligning device for laterally aligning a rail testing device with respect to a rail being tested with a carriage structure that moves along the rail and supports the ultrasonic aligning device and the rail testing device so that these can be laterally adjusted by an actuator, comprising:

an array of closely spaced ultrasonic transducer elements, with center to center distances between elements being selected to determine incremental lateral positions of the array relative to the rail; a wheel enclosing the array for being positioned on top of the rail with said array being aligned so as to be laterally with respect to said rail;

means for scanning the ultrasonic elements and causing the generation of ultrasonic beams towards the rail from respective ultrasonic elements and for detecting reflections caused by the beams from an interface on the bottom of the rail;

a reflection signal analyzer responsive to detected reflections from respective elements to determine the lateral position of the ultrasonic array relative to the rail and produce a position signal indicative thereof; and an actuator responsive to the position signal to laterally displace the rail testing device in a direction selected to align the rail testing device with the rail.

2. The ultrasonic aligning device defined in claim 1 wherein the reflection analyzer further includes means for determining which ultrasonic elements caused reflections from said interface and which elements failed to cause a said reflection during a scanning of the array of elements; and means for deriving from said determining means said position signal indicative of the amount of misalignment of said array with respect to said rail.

3. The ultrasonic aligning device defined in claim 2 wherein the reflection analyzer further includes means for scanning said ultrasonic elements in successive groups of a predetermined number of elements selected from the array.

4. The ultrasonic aligning device defined in claim 3 wherein said reflection analyzer further includes means for validating the reflection signals from the groups.

5. The ultrasonic aligning device defined in claim 3 wherein said scanning means scans consecutively located elements in said groups.

6. The ultrasonic aligning device defined in claim 1 wherein the array has a center, and wherein the reflection analyzer further includes means for generating said position signal from a detection during a said scan of a transition of reflections and an absence of reflections.

7. The ultrasonic aligning device defined in claim 1 wherein said array of elements is oriented within said wheel to direct beams of ultrasonic energy at a region of the base located below a web of the rail.

8. The ultrasonic aligning device defined in claim 1 wherein the reflection analyzer includes gating means for detecting reflections from said base region.

9. The ultrasonic aligning device defined in claim 8, wherein the gating means is of sufficient duration to accommodate a plurality of rail sizes.

10. The ultrasonic aligning device defined in claim 1 wherein the reflection analyzer includes software for analyzing detected reflections.

11. The ultrasonic aligning device defined in claim 10 wherein the software includes means for deriving valid reflections in accordance with criteria including definitive patterns, selected from the group consisting of consecutive hits followed by consecutive non-hits, consecutive non-hits followed by consecutive hits, and consecutive non-hits followed by consecutive hits followed by consecutive non-hits.

12. An ultrasonic aligning device for laterally aligning a rail testing device with respect to a rail being tested with a carriage structure that moves along the rail and laterally moveably supports the ultrasonic aligning device and the rail testing device, comprising:

an ultrasonic transducer formed of an array of closely spaced ultrasonic elements, with center to center distances between elements being selected to determine incremental lateral positions of the array relative to the rail; the array being oriented to be positioned opposite the top of the rail with a predetermined lateral alignment relative to the rail;

an ultrasonic element activating and receiver circuit to cause the generation of ultrasonic beams towards the rail and formed by selectively actuated ultrasonic elements extending across the array and produce echo signals representative of the incidence of the ultrasonic beam onto a base portion of the rail;

an echo analyzer responsive to echo signals representative of acoustic reflections of the base portion to determine the lateral position of the ultrasonic array relative to the rail and including a computer;

a software executing on a computer for validating at least one group of predetermined base patterns to enable the echo analyzer to produce a position signal indicative of the lateral position of the ultrasonic array; and storing signals indicative of reflections and an absence of reflections with said interface as a function of said elements;

deriving from said stored signals a position signal indicative of the alignment of the array relative to said rail; and laterally moving said rail testing device in a direction so as to reduce the position signal and align the rail testing device with said rail.

13. The ultrasonic alignment device defined in claim 12 wherein the carriage structure includes first and second probe wheels, which are ultrasonically aligned with respectively parallel rails, the actuator being a hydraulic actuator.

14. The ultrasonic alignment device defined in claim 13 wherein each of the first and second probe wheels is provided with an array of acoustic elements.

15. The ultrasonic aligning device defined in claim 13 and further including validation means for confirming a valid scanning of elements with criteria selected from the group consisting of consecutive hits followed by consecutive non-hits, consecutive non-hits followed by consecutive hits, and consecutive non-hits followed by consecutive hits followed by consecutive non-hits.

16. A method for laterally aligning a rail testing device with respect to a rail being tested with a carriage structure that moves along the rail and laterally moveably supports an ultrasonic aligning device and a rail testing device, comprising the steps of:

moving an array of ultrasonic elements along the top of the rail with the array directed to inject ultrasonic beams into the rail through a web of the rail and onto its base and with the array oriented laterally with respect to the longitudinal dimension of the rail;

while the array is moving, scanning the array by activating ultrasonic pulses from individual elements in the array and detecting acoustic reflections arising from an incidence of respective element beams onto an interface of the base of the rail;

storing signals indicative of reflections and an absence of reflections with said interface as a function of said elements;

deriving from said stored signals a position signal indicative of the alignment of the array relative to said rail; and laterally moving said rail testing device in a direction so as to reduce the position signal and align the rail testing device with said rail.

17. The method defined in claim 16 wherein said scanning step comprises the steps of:

activating elements in the array in predetermined successively located groups and detecting reflections attributable to elements activated in said groups.

18. The method defined in claim 16 wherein said deriving step includes the steps of determining whether stored reflections from the scanning of said array include a first pattern consisting of consecutive hits followed by consecutive non-hits, determining whether stored reflections include a second pattern consisting of consecutive non-hits, followed by consecutive hits, determining whether stored reflections include a third pattern consisting of consecutive non-hits, followed by consecutive hits, followed by consecutive non-hits, validating said scanning step when any one of said patterns has been determined to be present in said stored reflections.

19. The method defined in claim 16 wherein said deriving step further includes the steps of:

determining the element in the array for which a stored reflection or absence thereof is indicative of a transition identifying a side of a web in the rail and generating said position signal therefrom.

20. The method defined in claim 16 wherein said deriving step further includes the steps of:

determining the elements in the array for which stored reflections or absences thereof are indicative of transitions identifying opposite sides of a web in the rail and generating said position signal therefrom.

* * * * *